MILKWEED PLANT

Filed May 18, 1971 2 Sheets-Sheet 1

INVENTOR
BARNELL L. COBIA
BY Roger L. Martin
ATTORNEY

INVENTOR
BARNELL L. COBIA

BY Roger L. Martin
ATTORNEY

United States Patent Office

Plant Pat. 3,306
Patented Feb. 20, 1973

3,306

MILKWEED PLANT

Barnell L. Cobia, 135 Temple Grove Drive,
Winter Garden, Fla. 32787

Filed May 18, 1971, Ser. No. 144,694
Int. Cl. A01h 5/00
U.S. Cl. Plt.—88 1 Claim

ABSTRACT OF THE DISCLOSURE

A new and distinct plant variety of the milkweed family is principally distinguished from its antecedents and known related varieties by a growth habit providing specimens which have leaf blades that are characteristically curled transversely of the midrib, which have stems that in color are dominated by red, red-purple and yellow-red hues, which have petioles and peduncles that in color are dominated by relatively long lasting red and red-purple hues, which have leaf blades that are variegated in patterns normally identifiable with those of the *Hoya carnosa compacta* (cv) Marginalis variety and have a green center field which is characteristically overcast in color dominated by relatively long lasting red, red-purple and yellow-red hues with generally low value and low chroma and a surrounding albino border area that in color is dominated by relatively long lasting red-purple, red and yellow-red hues of generally higher value and chroma than encountered in the green center field, and which have an inflorescence with sepals and petals having attractive colors dominated by red-purple hues.

The invention relates to a new and distinct plant variety of the milkweed (Asclepiadaceae) family and which has been named the *Hoya carnosa compacta* (cv) Regalis by the inventor.

Certain plant specimens of the milkweed family are well known in the foliage plant market and among these are specimens of the *Hoya carnosa compacta* variety. Plants of this variety have a compact growth habit and a leaf blade with a solid green field which encompasses the entire upper epidermal area of the blade, the leaf blade being characterized in the compact growth habit of the plant by a pronounced tendency to curl along the midrib so that the upper epidermal part comes generally into facial confrontation.

A lesser known variety related to the *Hoya carnosa compacta* variety is the *Hoya carnosa compacta* (cv) Mauna Loa variety which forms the subject matter of the inventors co-pending application Ser. No. 808,025, filed Mar. 13, 1969. Plant specimens of this variety are structurally closely similar in appearance to plant specimens of the *Hoya carnosa compacta* variety but are readily distinguishable from the latter variety by characteristics which, among others, provide variegated leaf blades that have an albino center field which is surrounded by a green border area.

Among new plant varieties of the milkweed family which have yet to be introduced in the marketplace is the *Hoya carnosa compacta* (cv) Marginalis variety which forms the subject matter of an application for U.S. Letters Patent filed substantially simultaneously with the current application. Plant specimens of this variety are structurally similar to plant specimens of the *Hoya carnosa compacta* variety but are principally distinguished from the latter variety by variegated leaf blades which provide solid green center fields in the blade and which are surrounded by an albino border area.

Also related to the above named plant varieties is the new and distinct variety which has been named the *Hoya carnosa* (cv) Tricolor by the inventor and which forms the subject matter of Plant Patent No. 2950. Plant specimens of this variety are similar in structural appearance to specimens of the *Hoya carnosa* Variegata variety but may be distinguished by certain relatively long lasting colors which are dominated by red and red-purple hues in the albino border areas of the leaf blades among other parts of the plant specimens.

The principal object of the invention has been to develop a new plant variety having the compact growth habit characteristic of specimens of the *Hoya carnosa compacta* variety which exhibit variegated leaf blade patterns like or similar to those appearing in plant specimens of the *Hoya carnosa compacta* (cv) Marginalis variety and which in addition thereto exhibits color characteristics in the leaf blade that are like or similar to those exhibited by the *Hoya carnosa* (cv) Tricolor variety. This object of the invention has been fully realized as will be evident from the following detailed disclosure.

Plant specimens of the new variety have the compact growth habit characteristic of specimens of the *Hoya carnosa compacta* variety and are structurally similar in appearance except that the leaf blades are characteristically curled transversely of the midrib and backwards so that the upper epidermal parts of the blade generally face outwardly in the curled form of the leaf. Apart from the structurally characteristics of the new variety, the leaf blades are variegated in patterns which are normally identifiable with the *Hoya carnosa compacta* (cv) Marginalis variety but are nevertheless distinguishable from this variety by a green center field that is overcast with color dominated by relatively long lasting red, red-purple and/or yellow-red hues of generally low value and low chroma and by relatively long lasting red-purple, red and yellow-red hues of generally higher value and higher chroma than encountered in the green center field. These long lasting color characteristics are normally identifiable with specimens of the *Hoya carnosa* (cv) Tricolor variety and like this last named variety, plant specimens of the new variety also have petioles and peduncles which in color are dominated by relatively long lasting red and/or red-purple hues of generally low value and low chroma and have an inflorescence with sepals and petals that have attractive colors which are principally dominated by red-purple hues. Stems of the new variety are further characterized by color dominated by red, red-purple and yellow-purple hues.

The new variety appeared as a sport on a plant specimen of the *Hoya carnosa compacta* (cv) Marginalis variety which was under cultivation in a nursery at Winter Garden, Fla., and since the initial discovery of the new variety, has been asexually reproduced by the inventor at the Winter Garden nursery by the propagation of stem cuttings taken from the original plant specimen. Through successive propagations it has been ascertained that the new variety is mainly distinguished from its antecedents and related varieties known to the inventor by a growth habit providing specimens which combine the characteristics herein mentioned.

The accompanying drawings serve, by color photographic means, to illustrate the new variety and wherein.

Figure 1:
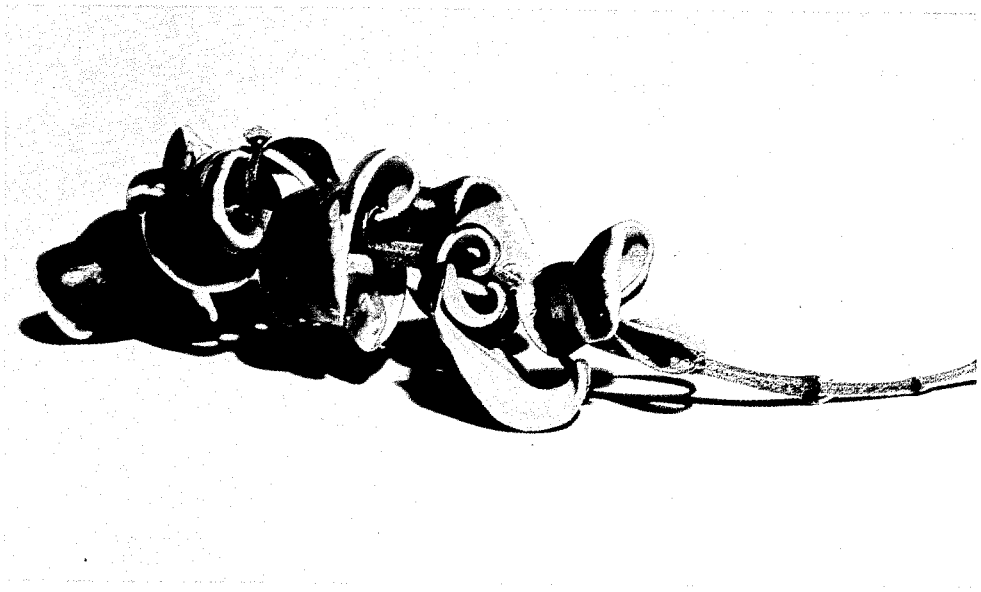
FIG. 1 is a color photograph of a plant specimen of the new variety.
Figure 2:
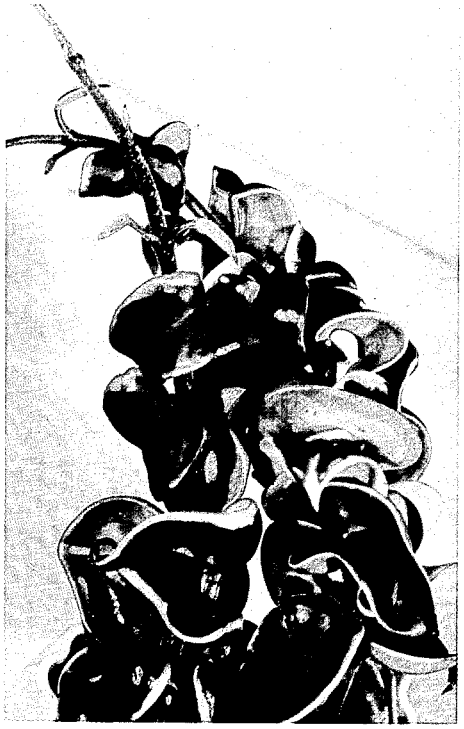
FIG. 2 is a color photograph of a vine cut from a plant specimen of the new variety as seen in comparison with a vine cut from a plant specimen of the *Hoya carnosa compacta* (cv) Marginalis variety.
Figure 5:
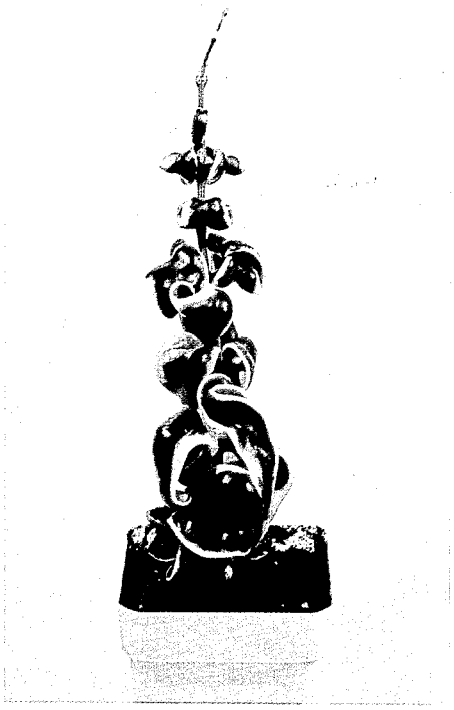
FIG. 5 is a color photograph of a vine cutting showing a peduncle on a plant specimen of the new variety.
Figure 3:
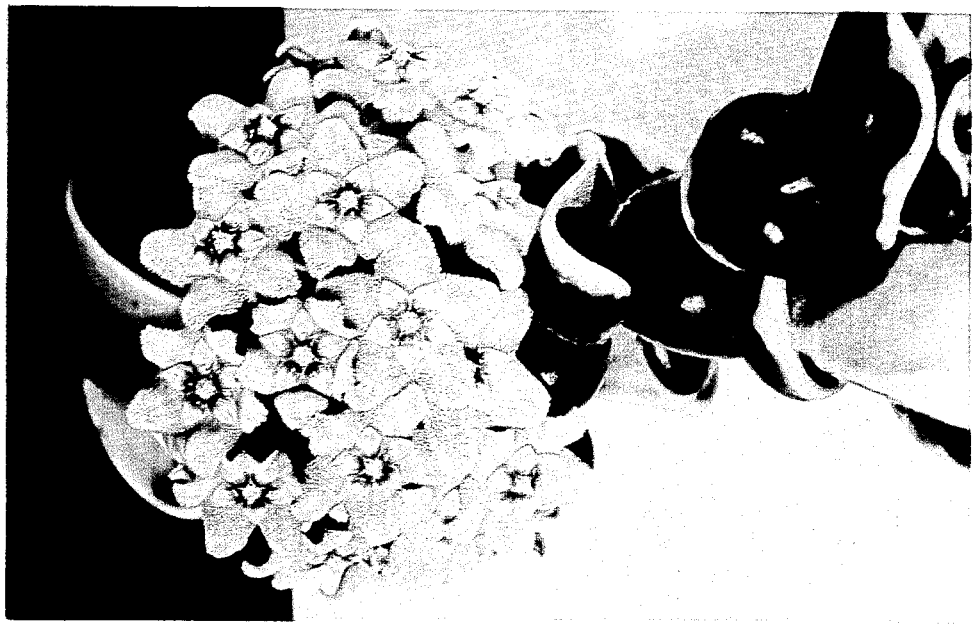
FIG. 3 is a color photograph showing an inflorescence on a vine of the new variety.
Figure 4:
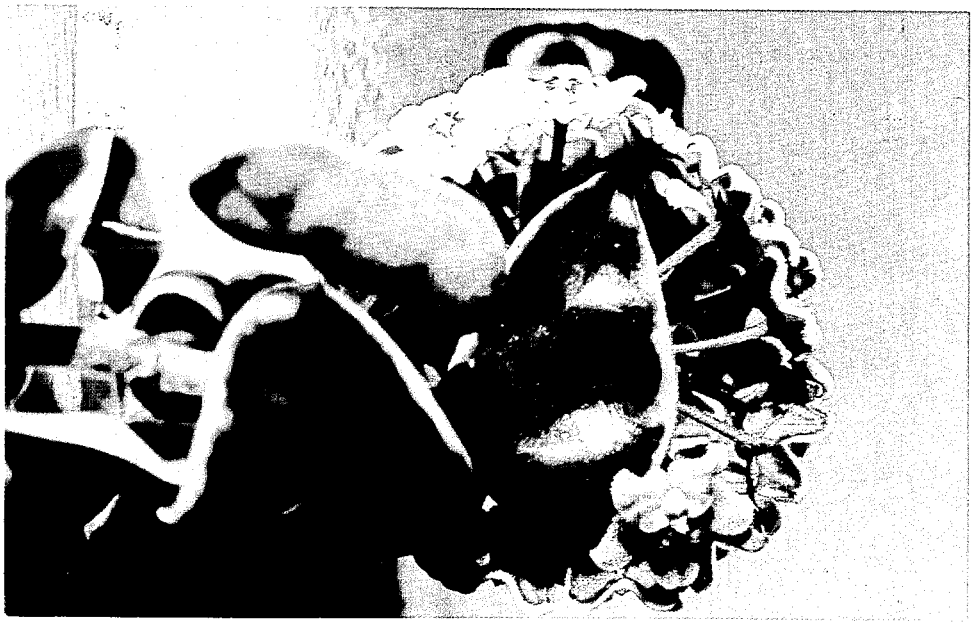
FIG. 4 is a color photograph of the inflorescence seen in FIG. 3 as taken to show the underside of the flowers.

The following is a detailed description of the new plant variety with colors, unless otherwise clearly indicated by the text, being named in accord with the ISCC-NBS method of designating colors (U.S. Department of Commerce, National Bureau of Standards, Circular 553, issued Nov. 1, 1955), the named colors being interpreted from color notations derived by comparison with color specimens in the current "Neighboring Hues Edition" of the Munsell Book of Color, published by the Munsell Color Company, Inc., of Baltimore, Md. On the other hand, when reference is made to hues, values and chroma, reference is being made to the Munsell hues, values and chromas.

*Plant description*

Name: *Hoya carnosa compacta* (cv) Regalis.

Origin: A sport on a plant specimen of the *Hoya carnosa compacta* (cv) Marginalis variety.

Classification:

(*A*) *Botanic.*—(Asclepiadaceae) milkweed family.

(*B*) *Commercial.*—Foliage plant.

Form: Semisucculent, tropical, twining vine type perennial evergreen with some branching.

Stems:

(*A*) *General.*—Caulescent, fleshy, herbaceous with structural characteristics normally identifiable with the *Hoya carnosa compacta* variety.

(*B*) *Texture.*—Moderately pubescent during immaturity and with age becoming glaucous and ultimately covered with thick waxy scale.

(*C*) *Size.*—(1) Diameter: usually between 2 and 6 mm. for mature stems during the first year of vine growth from break. (2) Internode: usually between 8 and 30 mm. for mature stems during the first year of vine growth from break.

(*D*) *Color.*—Characteristically dominated by a relatively long lasting red and red-purple hues of generally low value and low chroma before fading and becoming obscured by waxy scale formations. Commonly occurring colors are dark grayish purple (7.5 RP 3/2) (near 7.5 RP 2/2) (10 RP 3/2) (near 10 RP 2/2), dark purplish red (10 RP 3/6) (near 7.5 RP 2/2) (near 10 RP 2/2), blackish purple (near 7.5 RP 2/2) (near 10 RP 2/2) (near 10 RP 2/1), very dark purplish red (near 7.5 RP 2/2) (near 10 RP 2/2), purplish gray (10 RP 3/1), blackish red (near 2.5 R (2/2), very dark red (near 2.5 R (2/2) (near 5 R 2/2), purplish black (10 RP 2/1), dark grayish red (5 R 3/2) (2.5 R 3/2) (near 2.5 R 2/2) (near 5 R 2/2), blackish red (near 5 R 2/2) dark red (5 R 3/4), dark grayish reddish brown (7.5 R 2/2) (10 R 2/1) (10 R 2/2) (2.5 YR 2/2), grayish reddish brown (10 R 4/2) (7.5 R 3/2) (2.5 YR 4/2) (2.5 YR 3/2), dark grayish yellowish brown (10 YR 3/2) (10 YR 2/1) and grayish brown (5 YR 3/2 (7.5 YR 4/2) before fading and ultimately becoming obscured by waxy scale formations.

Leaves:

(*A*) *General.*—Simple exstipulate with structural characteristics normally identifiable with *Hoya carnosa compacta* variety except for blade curling tendencies referred to infra.

(*B*) *Arrangement.*—Opposite.

(*C*) *Margins.*—Entire.

(*D*) *Venation.*—Pinnate.

(*E*) *Shape.*—(1) General: predominately ovate and elliptic with occasional variations. (2) Leaf apices: usually acute with some acuminate occurrences. (3) Leaf bases: usually from obtuse to cordate with some acute occurrences.

(*F*) *Petioles.*—(1) General: fleshy. (2) Texture: slightly pubescent and with age becoming glaucous and ultimately covered with thick waxy scale. (3) Size: (a) Diameter—usually between 1 and 4 mm. for mature petioles during first year of growth. (b) Length—usually between 4 and 12 mm. for mature petioles during first year of growth. (4) Color: characteristically dominated at exposed side of petiole by relatively long lasting red and red-purple hues of generally low value and low chroma before fading and becoming glaucous. Commonly occurring colors in young mature growth less than 6 months old are grayish purplish red (7.5 RP 4/4) (7.5 RP 5/6) (7.5 RP 4/6), dark purplish red (10 RP 3/4) (7.5 RP 3/4) (7.5 RP 3/6) (near 10 RP 2/2), dark grayish purple (10 RP 3/2) (7.5 RP 3/2) (near 10 RP 2/2), blackish purple (near 10 RP 2/2), very dark purplish red (near 10 RP 2/2), blackish red (near 2.5 R 2/2), very dark red (near 2.5 R 2/2), dark red (2.5 R 3/6) (2.5 R 3/4) (5 R 3/4), dark grayish red (2.5 R 3/2) (near 2.5 R 2/2) (5 R 3/2), grayish red (5 R 4/4) (2.5 R 5/6), grayish reddish brown (10 R 3/2) and dark grayish reddish brown (10 R 2/2). Commonly occurring colors in older growth and at stem sides of petioles in younger growth are light grayish red (5 R 6/4), moderate reddish brown (2.5 YR 4/4), moderate brown (5 YR 4/4) (7.5 YR 4/4), moderate yellowish brown (10 YR 4/4), moderate olive brown (2.5 Y 4/4), moderate olive (5 Y 4/4) (7.5 Y 4/4), light olive (7.5 Y 5/4) (10 Y 5/4) (10 Y 5/6) (10 Y 6/4), moderate pink (2.5 R 6/4), moderate yellow green (2.5 GY 6/6) (2.5 GY 5/6) and moderate yellow (2.5 GY 7/6).

(G) *Leaf blades.*—(1) General: semisucculent with characteristic tendency to curl transversely of the midrib and backwardly so that the upper epidermal part of the blade faces outwardly in the curled form of the leaf, and distinctively characterized by variegated leaf blade pattern identifiable with the *Hoya carnosa compacta* (cv) Marginalis variety to provide in the upper epidermal blade part a green center field area which is surrounded by an albino border area and in the lower epidermal blade part with an albino border area which surrounds a green center field area and further characterized in the upper epidermal part by a green center field that is overcast with color dominated by relatively long lasting red, red-purple and yellow-red hues of generally low value and low chroma and a surrounding albino border area that in color is dominated by relatively long lasting red-purple, red and yellow-red hues of generally higher value and high chroma than encountered in the green center field. (2) Texture: (a) Upper epidermal part—slightly pubescent during immaturity and with smooth waxy appearing surface during maturity. (b) Lower epidermal part—moderately pubescent and heavily glaucous at maturity. (3) Size: (a) Length—usually between 30 and 70 mm. during first year of maturity. (b) Maximum width—usually between 20 and 45 mm. during first year of maturity. (4) Color: (a) Upper epidermal blade part—(1) Green center field area: commonly occurring overcast colors in immature and young mature growth less than about 40 days old are blackish purple (near 10 RP 2/2), dark grayish purple (near 10 RP 2/2), dark purplish red (near 10 RP 2/2), very dark purplish red (near 10 RP 2/2), dark grayish red (near 2.5 R 2/2), blackish red (near 2.5 R 2/2), very dark red (near 2.5 R 2/2), dark grayish reddish brown (2.5 YR 2/2) (7.5 R 2/2) (10 R 2/2), grayish reddish brown (2.5 YR 3/2), grayish brown (5 YR 3/2) (7.5 YR 3/2), brownish gray (5 YR 3/2), moderate olive brown (2.5 Y 3/2) and grayish olive (5 Y 3/2) while commonly occurring colors after fading in the older growth are moderate yellow green (2.5 GY 6/6) (2.5 GY 5/6), strong yellow green (5 GY 6/8) (near 5 GY 5/6) and moderate olive green (7.5 GY 4/6) (7.5 GY 4/4) (5 GY 5/6). (2) Albino border area: commonly occurring colors in immature and young mature growth less than 60 days old are dark purplish pink (7.5 RP 6/8), moderate purplish pink (7.5 RP 7/6) (7.5 RP 7/8), pale purplish pink (7.5 RP 8/4), dark purplish red (10 RP 3/6), grayish purplish red (10 RP 4/4) (10 RP 4/6), moderate purplish red (10 RP 4/8) (10 RP 5/8) (10 RP 4/10) (10 RP 5/10), deep pink (10 RP 6/8) (10 RP 6/10) (5 R 6/8) (2.5 R 6/8), moderate pink (10 RP 7/6) (near 10 RP 8/6) (10 RP 7/4) (near 2.5 R 8/4) (near 5 R 8/4) (5 R 7/6), strong pink (10 RP 7/8) (2.5 R 7/8), light pink (near 10 RP 8/6) (near 2.5 R 8/4) (near 5 R 8/4), pale pink (5 R 9/2), moderate yellowish pink (near 5 YR 7/6) (near 2.5 YR 7/6), moderate orange (near 5 YR 7/6) (near 2.5 YR 7/6), pale orange yellow (near 7.5 YR 8/6), light orange yellow (near 7 YR 8/6) and moderate orange yellow (near 7.5 YR 8/6). Commonly occurring colors after fading in older growth are pale yellow (2.5 Y 9/4) (near 7.5 Y 9/2) (5 Y 9/4), pale yellow green (10 Y 9/2), pale greenish yellow (10 Y 9/4) (7.5 Y 9/4), light greenish yellow (10 Y 9/8) (7.5 Y 9/6), light yellow (2.5 Y 9/6) and yellowish white (near 7.5 Y 9/2) (10 Y 9/1). (b) Lower epidermal part—(1) Green center field: usually moderate yellow green (2.5 GY 6/4) (5 GY 6/4) (5 GY 7/4), grayish yellow green (2.5 GY 6/2) and light green (5 GY 7/4) in mature growth. (2) Albino border area: commonly occurring colors in immature and young mature growth less than 60 days old are moderate red (2.5 R 4/8) (2.5 R 4/10), moderate purplish red (10 RP 5/8) (10 RP 4/8), grayish purplish red (10 RP 5/6), deep pink (2.5 R 6/8) (5 R 6/10), strong yellowish pink (7.5 R 7/8), light yellowish pink (near 10 R 8/4) (near 2.5 YR 8/4) and moderate yellowish pink (near 10 R 8/4) while commonly occurring colors after fade-out in older growth are pale greenish yellow (7.5 Y 9/4) (10 Y 9/4), light greenish yellow (7.5 Y 9/6), pale yellow green (10 Y 9/2), yellowish pink (near 10 R 8/4), moderate yellowish pink (near 10 R 8/4), light grayish yellow (7.5 Y 9/6), light yellow (5 Y 9/6), moderate yellow green (5 GY 6/4), yellowish white (near 7.5 Y 9/2) (5 Y 9/2) and pale yellow (2.5 Y 9/4) (near 7.5 Y 9/2).

Inflorescence: Has structural characteristics normally identifiable with *Hoya carnosa compacta* variety.

(*A*) *Form*—Simple umbel with minute 5-merous bracts and usually 20 to 45 flowers in a cluster.

(*B*) *Peduncles*.—(1) General: hard, fleshy. (2) Texture: slightly pubescent and with age becoming glacous and ultimately covered with thick waxy scale.(3) Size: (a) Length—usually between 5 and 15 mm. at maturity. (b) Diameter—usually between 1 and 4 mm. at maturity. (c) Color—characteristically dominated by relatively long lasting red and red-purple hues of generally low value and low chroma before fading and becoming obscured by waxy scale formations. Commonly occurring colors are dark purplish red (10 RP 3/4) (7.5 RP 2/2) (10 RP 3/6), dark red (2.5 R 3/4) (5 R 3/4), very dark purplish red (near 7.5 RP 2/2), dark grayish purple (near 7.5 RP 2/2) and moderate reddish brown (7.5 R 3/4) prior to becoming glaucous.

(C) *Pedicels*.—(1) General: soft, fleshy. (2) Texture: sparsely pubescent. (3) Size: (a) Length—usually between 15 and 28 mm. at maturity. (b) Diameter—usually between .7 and 1.7 mm. at maturity. (4) Color: commonly dark pink (10 RP 6/6), dark purplish red (7.5 RP 3/6), moderate purplish red (10 RP 4/10) (10 RP 4/8) (7.5 RP 4/8), grayish red (7.5 R 4/6) (2.5 R 4/6) (5 R 4/6) and grayish purplish red (10 RP 4/6).

(D) *Flowers*.—(1) General: complete, perfect, actinomorphic and 5-merous type flower with hypogynous perianth and alternate sepal-petal and petal-corona segment arrangements. (2) Size: usually between 12 and 18 mm. in overall diameter. (3) Calyx: (a) General—5-merous with separate, valvate sepals. (b) Sepal texture—(1) Upper epidermis: smooth, glabrous. (2) Lower epidermis: sparsely pubescent. (c) Sepal size—proximal to distal end length is usually about 2.5 to 3.0 mm. (d) Sepal color—characteristically dominated by red-purple hues and commonly dark pink (10 RP 6/6), dark purplish red (10 RP 3/4) (10 RP 3/6), grayish purplish red (10 RP 4/4 (10 RP 4/6) (7.5 RP 4/4) (7.5 RP 4/6) (10 RP 5/6) (10 RP 3/10) and dark grayish purple (7.5 RP 3/2) (7.5 RP 2/2) (7.5 RP 2/2). (4) Corolla: (a) General—5-merous, valvate and rotate with interpetal basal fusion for about ½ petal length. (b) Petal texture—(1) Upper epidermis: very dense velvety pubescence. (2) Lower epidermis: glaucous and waxy. (c) Petal size—proximal to distal and length usually about 6 to 7 mm. (d) Petal color—characteristically dominated by red-purple hues. (1) Upper epidermal side: commonly dark pink (10 RP 6/6), dark purplish pink (5 RP 6/8) (7.5 RP 6/), moderate pink (10 RP 7/4) (7.5 RP 7/6), light grayish purplish red (10 RP 6/4), grayish purplish red (10 RP 5/4) (10 RP 4/6) and moderate purplish pink (5 RP 7/6). (2) Lower epidermal side: commonly dark purplish red (7.5 RP 3/6) (5 RP 3/8), moderate purplish red (7.5 RP 4/8) (10 RP 4/10) (5 RP 5/8) (7.5 RP 5/8), grayish purplish red (5 RP 4/6) (5 RP 5/6 (10 RP 4/6) (7.5 RP 5/6) (10 RP 5/6) (7.5 RP 4/6) and moderate purplish pink (7.5 RP 3/6). (5) Corona: (a) General—5-merous, horn-like segments which are adnate to stigma and corolla and crested at their proximal ends. (b) Segment texture—hard, smooth, waxy and glabrous. (e) Segment color—(1) Proximal end: commonly dark purplish red (7.5 RP 3/6) (10 RP 3/6) (7.5 RP 3/4) (5 RP 3/4), grayish purplish red (10 RP 4/6), moderate purplish red (10 RP 4/8) and merging with distal end color. (2) Distal end: commonly yellowish white (10 Y 9/1) (7.5 Y 9/1) (5 Y 9/1) (near 7.5 Y 9/2) (near Y 9/2), pale yellow green (10 Y 9/2), pale yellow (near 7.5 Y 9/2) (near 5 Y 9/2) and merging with proximal end color. (6) Androecium: (a) General—5-merous pollinium pairs partially enclosed by an expanded translucent parenchymatous translators and attached to stigma through corpuscula located between adjacent segments and with pollinia and translators rising above corpuscula and stigma in converging conical arrangement. (b) Pollinium color—commonly vivid yellow (2.5 Y 8/10) and/or brilliant yellow (2.5 Y 8/10). (7) Gyneocium: (a) General—compound and apocarpous pistil with common stigma. (b) Stigma—(1) General: 5-lobed and waxy. (2) Color: commonly light yellow (near 2.5 Y 8/8) (near 5 Y 9/8), brilliant yellow (near 5 Y 9/8) and/or moderate yellow (near 2.5 Y 8/8). (c) Style—lacking. (d) Ovary—(1) General: two monocarpellate ovularies with axilarry placentation of ovules. (2) Color: usually dark purplish red (10 RP 3/6).

The above description is based on observations of well fertilized plants of less than two years old from initial propagation and which were grown under 85% shaded nursery conditions in the Winter Garden, Fla., area and wherein temperatures range approximately from 60–85° F. during the winter months and from 75–95° F. during the summer months.

The following is a general description of a plant of the new variety which was propagated from a stem cutting, the description being taken in the month of January, about thirteen months after the cutting was first planted in a nursery at Winter Garden, Fla.

Stem:

(*A*) *Length.*—About 38 mm. from break to tip.

(*B*) *Number of nodes.*—18 mature plus 3 with embryonic leaves.

(*C*) *Diameter.*—Ranges from 1 mm. at tip to about 4 mm. near the rooted cutting.

(*D*) *Internode distance.*—Varies from about 5 mm. to about 21 mm.

(E) *Color.*—dark grayish reddish brown (10 R 2/2) (2.5 YR 2/2), grayish reddish brown (2.5 YR 3/2), grayish brown (5 YR 3/2) (7.5 YR 4/2), blackish purple (near 10 RP 2/1) (near 10 RP 2/2), purplish black (near 10 RP 2/1) and dark grayish purple (near 10 RP 2/1) in stem part less than 6 months old and moderate yellow green (5 GY 7/6) (5 GY 6/6) (2.5 GY 5/4) in older stem part not appreciably obscured by waxy scale.

Leaves:

(*A*) *Number of nonembryonic leaves.*—36 mature leaves plus 6 immature including 2 newly immature (less than 15 days old).

(*B*) *Petioles.*—(1) Diameter—vary from 1.5 to 3 mm. at maturity. (2) Length—vary from 6 to 10 mm. at maturity. (3) Color—blackish purple (near 10 RP 2/2), dark grayish purple (10 RP 3/2), dark purplish red (10 RP 3/4), dark red (2.5 R 3/4) (5 R 3/4) and grayish red (2.5 R 5/6) in growth less than 6 months old with moderate reddish brown (2.5 YR 4/4), light olive (10 Y 6/4), light grayish red (5 R 6/4), moderate pink (2.5 R 6/4) and moderate yellow (2.5 GY 7/6) commonly occurring in older growth and on stem side of petiole in younger growth.

(*C*) *Blades.*—(1) Maximum width—vary from 14 to 36 mm. at maturity. (2) Length—vary from 32 to 70 mm. at maturity. (3) Color—(a) Upper epidermal albino border area—moderate red (2.5 R 4/8) (2.5 R 4/10) (2.5 R 5/10) (2.5 R 5/8), deep pink (5 R 6/8), moderate pink (5 R 7/6), moderate yellowish pink (near 5 YR 7/6) and moderate orange (near 5 YR 7/6) in young mature growth less than 4 months old and pale yellow (5 Y 9/4), light greenish yellow (7.5 Y 9/6), yellowish white (near 7.5 Y 9/2) and pale yellow (near 7.5 Y 9/2) in faded older growth. (b) Upper epidermal green center field—overcast with dark grayish red (near 2.5 R 2/2), very dark red (near 2.5 R 2/2), brownish gray (5 YR 3/1) in growth less than 30 days old and moderate yellow green (5 GY 5/6) (7.5 GY 4/4), strong yellow green (5 GY 6/8) and moderate olive green (7.5 GY 4/6) after fading in older growth. (c) Lower epidermal border area—moderately red (2.5 R 4/8) (2.5 R 4/10), light yellowish pink (near 10 R 8/4), moderate yellowish pink (near 10 R 8/4) and deep pink (5 R 6/8) in growth less than 30 days old and yellowish pink (near 10 R 8/4), moderate yellowish pink (near 10 R 8/4), light yellow (5 Y 9/6), pale greenish yellow (7.5 Y 9/4), yellowish white (near 7.5 Y 9/2) and pale yellow green (10 Y 9/2) after fading in older growth. (d) Lower epidermal green center field—moderate yellow green (5 GY 7/4) (5 GY 6/4) in mature growth.

The following is a general description of a typical inflorescence which appeared on a vine about 2 years old.

Number of flowers: 25.

Peduncle:

(*A*) *Size.*—(1) Length: about 12 mm. (2) Diameter: about 2.5 mm. average.

(*B*) *Color.*—Very dark purplish red (near 7.5 RP 2/2).

Pedicels:

(*A*) *Size.*—(1) Length: varies from 19 to 21 mm. (2) Diameter: about 1 mm. in average.

(*B*) *Color.*—grayish purplish red (10 RP 4/6), grayish red (7.5 R 4/5) and light reddish brown (2.5 YR 5/4).

Flowers:

(*A*) *Size.*—15 to 16 mm. in diameter.

(*B*) *Sepal size.*—proximal to distal end length about 3 mm.

(*C*) *Sepal color.*—grayish purplish red (10 RP 4/4) (10 RP 4/6) (7.5 RP 4/4) (7.5 RP 4/6), dark purplish red (10 RP 3/6).

(*D*) *Petal size.*—proximal to distal end length about 5.5 mm.

(*E*) *Petal color.*—(1) Upper epidermal side: grayish purplish red (10 RP 5/4), dark pink (10 RP 6/6), dark purplish pink (7.5 RP 6/6), light grayish purplish red (10 RP 6/4) and moderate pink (10 RP 7/4). (2) Lower epidermal side: grayish purplish red (10 RP 4/6) (7.5 RP 5/6) (10 RP 5/6) (7.5 RP 4/6).

(*F*) *Corona segment color.*—(1) Proximal end: dark purplish red (10 RP 3/6), grayish purplish red (10 RP 4/6), moderate purplish red (10 RP 4/8) and merging with distal end color. (2) Distal end: pale yellow green (10 Y 9/2), yellowish white (near 7.5 Y 9/2) (near 5 Y 9/2) and pale yellow (near 7.5 Y 9/2) (near 5 Y 9/2).

(*G*) *Pollinium color.*—brilliant yellow (near 2.5 Y 8/8).

(*H*) *Stigma color.*—Moderate yellow (near 2.5 Y 8/6), light yellow (near 2.5 Y 8/6).

(*I*) *Ovary color.*—Dark purplish red (10 RP 3/4) (10 RP 3/6).

I claim:

1. The new and distinct variety of the milkweed family substantially as herein described and characterized in particular by a compact growth habit providing specimens which have leaf blades that are curled transversely of the midrib so that the upper epidermal parts of the blades generally face outwardly in the curled form of the leaves, which have stems that in color are dominated by long lasting red, red-purple and yellow-red hues, which have petioles and peduncles that in color are dominated by long lasting red and red-purple hues, which have an inflorescence with sepals and petals having attractive colors dominated by red-purple hues, and which have leaf blades that are variegated in patterns identifiable with specimens of the *Hoya carnosa compacta* (cv) Marginalis variety, the green center fields in the upper epidermal parts of the blade being overcast during immaturity and early maturity with color dominated by relatively long lasting red-purple, red and/or yellow-red hues of generally low values and low chroma and the albino border areas in the upper epidermal parts of the blades in color being dominated by relatively long lasting red-purple, red and yellow-red hues of generally higher value and higher chroma than encountered in the green center fields.

No references cited.

ROBERT BAGWILL, Primary Examiner

PO-1050
(5/69)

UNITED STATES PATENT OFFICE
CERTIFICATE OF CORRECTION

Patent No. Plant Patent No. 3306 Dated February 20, 1973

Inventor(s) Barnell L. Cobia

It is certified that error appears in the above-identified patent and that said Letters Patent are hereby corrected as shown below:

Column 4, Line 27, delete "(10 YR 4/4)" and substitute -- (10 YR 5/4) --;
Column 6, Line 30, delete "and" and substitute -- end --;
Line 34, delete "(7.5 RP";
Line 35, delete "6/)" and substitute -- (7.5 RP 6/6) --;
Line 54, delete "(near Y 9/2)" and substitute -- (near 5 Y 9/2) --;

Signed and sealed this 3rd day of July 1973.

(SEAL)
ttest:

DWARD M.FLETCHER,JR.
ttesting Officer

Rene Tegtmeyer
Acting Commissioner of Patents